United States Patent
Roslin et al.

(10) Patent No.: US 11,406,374 B2
(45) Date of Patent: Aug. 9, 2022

(54) HERNIA REPAIR DEVICE

(71) Applicant: THE FEINSTEIN INSTITUTES FOR MEDICAL RESEARCH, Manhasset, NY (US)

(72) Inventors: Mitchell Roslin, Armonk, NY (US); Derek Young, Dublin (IE); Conor Hand, Dublin (IE)

(73) Assignee: i360medical Ltd., Dublin (IE)

( * ) Notice: Subject to any disclaimer, the term of this patent is extended or adjusted under 35 U.S.C. 154(b) by 409 days.

(21) Appl. No.: 16/623,468

(22) PCT Filed: Jun. 19, 2018

(86) PCT No.: PCT/US2018/038314
§ 371 (c)(1),
(2) Date: Dec. 17, 2019

(87) PCT Pub. No.: WO2018/236892
PCT Pub. Date: Dec. 27, 2018

(65) Prior Publication Data
US 2020/0170638 A1   Jun. 4, 2020

Related U.S. Application Data

(60) Provisional application No. 62/521,924, filed on Jun. 19, 2017.

(51) Int. Cl.
*A61B 17/04*     (2006.01)
*A61B 17/00*     (2006.01)
(Continued)

(52) U.S. Cl.
CPC ...... *A61B 17/0469* (2013.01); *A61B 17/0057* (2013.01); *A61B 17/06004* (2013.01);
(Continued)

(58) Field of Classification Search
CPC ... A61F 2002/0072; A61B 2017/00986; A61B 2017/0472; A61B 2017/00367; A61B 17/0469
See application file for complete search history.

(56) References Cited

U.S. PATENT DOCUMENTS 5,364,408 A      11/1994  Gordon
5,830,125 A  *  11/1998  Scribner ............ A61B 17/0057
                                                                606/139
(Continued)

FOREIGN PATENT DOCUMENTS

CN      106 214 196 A      12/2016
EP      0 830 843 A1        3/1998
(Continued)

OTHER PUBLICATIONS

PCT International Search Report and Written Opinion report dated Aug. 9, 2018 in connection with PCT/US2018/038314.
(Continued)

*Primary Examiner* — Alexander J Orkin
(74) *Attorney, Agent, or Firm* — Amster, Rothstein & Ebenstein LLP

(57) ABSTRACT

A hernia repair device including a main body, a plurality of suture needle ports, a plurality of suture needles and a central shaft. The central shaft includes a retractable distal flange disposed at a distal end portion of the central shaft and defines a central channel extending through the main body. The suture needle ports are adjustable between a first configuration in which the suture needle ports are housed entirely within the main body and a second configuration in which the suture needle ports partially extend from the distal end portion of the main body. The suture needles are adjustable between a first configuration in which the suture needles are housed entirely within the suture needle ports and a plurality of second configurations in which the suture needles partially extend from distal end portions of the suture needle ports. A hernia repair mesh is attached to the plurality of suture needles.

15 Claims, 21 Drawing Sheets

(51) Int. Cl.
*A61B 17/06* (2006.01)
*A61F 2/00* (2006.01)

(52) U.S. Cl.
CPC .............. *A61B 2017/00367* (2013.01); *A61B 2017/00637* (2013.01); *A61B 2017/00986* (2013.01); *A61B 2017/0472* (2013.01); *A61B 2017/06057* (2013.01); *A61F 2002/0072* (2013.01)

(56) References Cited

U.S. PATENT DOCUMENTS

| | | | | |
|---|---|---|---|---|
| 5,964,773 | A | * | 10/1999 | Greenstein ........... A61B 17/062 606/147 |
| 6,358,258 | B1 | * | 3/2002 | Arcia ................. A61B 17/0469 606/139 |
| 2002/0068951 | A1 | * | 6/2002 | Burbank ............ A61B 17/0469 606/139 |
| 2006/0004409 | A1 | | 1/2006 | Nobis et al. |
| 2006/0095052 | A1 | * | 5/2006 | Chambers .......... A61B 17/0469 606/139 |
| 2010/0069930 | A1 | | 3/2010 | Roslin et al. |
| 2011/0178537 | A1 | | 7/2011 | Whitman |

FOREIGN PATENT DOCUMENTS

| | | |
|---|---|---|
| WO | 99/12480 A1 | 3/1999 |
| WO | 03/090628 A1 | 11/2003 |

OTHER PUBLICATIONS

Communication Supplementary European Search report dated Dec. 23, 2020 in connection with European Patent Application No. 18821449.8.

* cited by examiner

HERNIA REPAIR DEVICE

RELATED APPLICATIONS

This application is a U.S. national phase application of PCT International Application No. PCT/US18/38314, filed Jun. 19, 2018 and entitled HERNIA REPAIR DEVICE, which in turn claims priority to and the benefit of U.S. Provisional Application No. 62/521,924, filed Jun. 19, 2017 and entitled HERNIA REPAIR DEVICE, the contents of which are incorporated herein by reference in their entirety.

FIELD OF THE INVENTION

This disclosure is directed to methods and apparatus for hernia repair, and more particularly to methods and apparatus for hernia repair involving deployment and fixation of a hernia repair mesh.

BACKGROUND

A hernia is a weakness or hole within a patient's abdominopelvic wall that may allow internal organ tissue, such as intestines or bowel, to ex-filtrate the abdominal cavity through the herniation site and potentially become entrapped within the herniation site. Common types of hernias include umbilical, inguinal and ventral hernias.

A common surgical hernia repair technique involves introduction of a mesh within the abdominopelvic cavity over the herniation site, so as to add a reinforcing "patch" to the wall. The hernia repair mesh is spread over the herniation site and affixed to the parietal peritoneum layer of the patient's internal abdominal wall in abutting relationship. The mesh prevents organ tissue ex-filtration through the abdominal wall herniation site.

Hernia repair is most commonly performed using laparoscopic instruments and requires lateral incisions into the patient so that the repair mesh can be stretched over the herniation site prior to affixation to the patient's interior abdominal wall. It is difficult to tension a sheet of planar mesh across the patient's generally cylindrical, concave inner abdominopelvic wall via laterally oriented access points. Loose or flaccid mesh may not provide sufficient structural integrity for the hernia repair and may necessitate future revision surgery. Mesh that is not properly tensioned over and affixed to the parietal peritoneum layer of the abdominal wall might not have sufficient structural integrity to inhibit ex-filtration of internal organ tissue through the existing herniation site or under the marginal edges of the mesh patch.

Other hernia repair techniques involve implantation of planar prosthetic repair devices or other medical procedures that repair voids in patient tissue directly through the void and/or by lateral placement over the void. For example, some repair prosthesis devices include structural reinforcements or tacking barbs to enhance abutment of the device and the underlying patient tissue. Such devices generally incorporate umbrella like structures that are introduced into a patient's body cavity in a folded state. Once the structure is inserted into the patient's body cavity the umbrella or parachute structure is opened and pulled against the body cavity over the tissue void. Depending on the design, the umbrella supporting rib structure is left in situ or removed from the patient. Compared to laterally introduced laparoscopic instruments, such direct insertion instruments require less maneuvering to the tissue repair/implantation site. However, the umbrella-like ribs require relatively large free volumetric space between the viscera and body cavity walls so that the umbrella may deploy.

SUMMARY OF THE INVENTION

An object of the present invention is to provide a minimally invasive hernia repair procedure and apparatus that minimizes the need for lateral incisions in a patient, and that preferably allows direct repair at the herniation site, with tensioned deployment and fixation of the repair prosthetic device to the patient's tissue at the implantation site.

A hernia repair device according to an exemplary embodiment of the present invention comprises: a main body comprising a first longitudinally extending slot and a second longitudinally extending slot, each of the first and second longitudinally extending slots comprising a first widened portion that forms a first locking slot and a second widened portion that forms a second locking slot, the second locking slot disposed at a more distal position along the main body relative to the first locking slot; a central shaft extending through the main body and comprising a retractable distal flange disposed at a distal end portion of the central shaft, the central shaft defining a central channel extending through the main body; a pair of distal flange switches, each distal flange switch comprising: a first portion fixed to the central shaft; and a second portion pivotally attached to the first portion and extending through a corresponding one of the first and second longitudinally extending slots, the second portion comprising a detent portion that is biased inwards, wherein the distal flange switch has a first locked configuration in which the detent portion protrudes into the first locking slot of the corresponding one of the first and second longitudinally extending slots, the distal flange switch has a second locked configuration in which the detent portion protrudes into the second locking slot of the corresponding one of the first and second longitudinally extending slots, adjustment of the distal flange switch from the first locked configuration to the second locked configuration results in deployment of the distal flange, and adjustment of the distal flange switch from the second locked configuration to the first locked configuration results in retraction of the distal flange; a plurality of suture needle ports that are adjustable between a first configuration in which the suture needle ports are housed entirely within the main body and a second configuration in which the suture needle ports partially extend from the distal end portion of the main body; a plurality of suture needles that are adjustable between a first configuration in which the suture needles are housed entirely within the plurality of suture needle ports and a plurality of second configurations in which the plurality of suture needles partially extend from distal end portions of the plurality of suture needle ports; and a hernia mesh attached to the plurality of suture needles.

According to an exemplary embodiment, the hernia repair device further comprises a suture needle port switch slideably disposed on the main body and attached to the plurality of suture needle ports so that movement of the suture needle port switch along the main body results in adjustment of the plurality of suture needle ports between the first and second configurations.

According to an exemplary embodiment, the main body further comprises a number of additional longitudinally extending slots so that a total number of longitudinally extending slots in the main body is equal to a number of suture needles that make up the plurality of suture needles.

According to an exemplary embodiment, each of the first and second longitudinally extending slots comprise a third widened portion that forms a third locking slot and a fourth widened portion that forms a fourth locking slot, the fourth locking slot disposed at a more distal position along the main body relative to the third locking slot.

According to an exemplary embodiment, each additional longitudinally extending slot comprises a first widened portion that forms a first locking slot and a second widened portion that forms a second locking slot, the second locking slot of each additional longitudinally extending slot disposed at a more distal position along the main body relative to the first locking slot of each additional longitudinally extending slot.

According to an exemplary embodiment, the hernia repair device further comprises a plurality of suture needle locking slots which include the third and fourth locking slots of the first and second longitudinally extending slots and the first and second locking slots of the additional longitudinally extending slots.

According to an exemplary embodiment, each of the plurality of suture needle ports comprises a suture needle access slot.

According to an exemplary embodiment, the hernia repair device further comprises: a plurality of suture needle switches, each of the plurality of suture needle switches comprising: a first portion fixed to a corresponding one of the suture needles; and a second portion pivotally attached to the first portion and extending through the suture needles access slot of a corresponding one of the suture needle ports, the second portion comprising a detent portion that is biased inwards, wherein the suture needle switch has a first locked configuration in which the detent portion protrudes into one of the suture needle locking slots of the corresponding one of the first, second and additional longitudinally extending slots, the suture needle switch has a second locked configuration in which the detent portion protrudes into another one of the suture needle locking slots of the corresponding one of the first, second and additional longitudinally extending slots, movement of the suture needle switch to the first locked configuration results in adjustment of the corresponding suture needle to one of the plurality of second configurations, and movement of the suture needle switch to the second locked configuration results in adjustment of the corresponding suture needle to another one of the plurality of second configurations.

According to an exemplary embodiment, each of the plurality of suture needle ports comprises a light source disposed at a distal end portion of the suture needle port.

According to an exemplary embodiment, the light source is a light-emitting diode.

According to an exemplary embodiment, the hernia repair device further comprises a hernia mesh cartridge slideably attached to the main body and that houses the hernia mesh in a rolled-up configuration, wherein movement of the main body relative to the hernia mesh cartridge results in pushing of the hernia mesh from the hernia mesh cartridge to an unrolled deployed configuration.

According to an exemplary embodiment, the hernia mesh cartridge comprises a proximal flange that operates with the distal flange to anchor the hernia repair device in position.

According to an exemplary embodiment, the central channel is configured to direct pressurized gas to the hernia mesh.

According to an exemplary embodiment, the central channel is configured to direct a camera through the hernia repair device to a hernia repair site.

According to an exemplary embodiment, the hernia repair device further comprises a quick release mechanism disposed on the main body at a more distal position relative to the plurality of suture needle port switches and the plurality of suture needle switches, wherein movement of the quick release mechanism towards a proximal end portion of the main body results in simultaneous retraction of the plurality of suture needles into the plurality of suture needle ports and the plurality of the suture needle ports into the main body.

BRIEF DESCRIPTION OF THE DRAWINGS

The above and related objects, features and advantages of the present invention will be more fully understood by reference to the following, detailed description of the preferred, albeit illustrative, embodiments of the present invention when taken in conjunction with the accompanying figures, wherein.

DETAILED DESCRIPTION OF THE INVENTION

The apparatus and methods of the present invention enable deployment of hernia repair surgical mesh or other prosthetic devices directly at the patient's implantation site, tensioning, including circumferential tensioning of the prosthesis to assure tight abutment against the patient's tissue at the implantation site, and secure affixation to the patient's tissue.

For the purposes of the present description, the terms "proximal" and "distal" refer to positions along a device or device component from the point of view of the clinician using the device, so that proximal portions of a device or device component are positioned closer to the clinician (and further from the patient) during a procedure as compared to distal portions of the device or device component.

Figure 1:
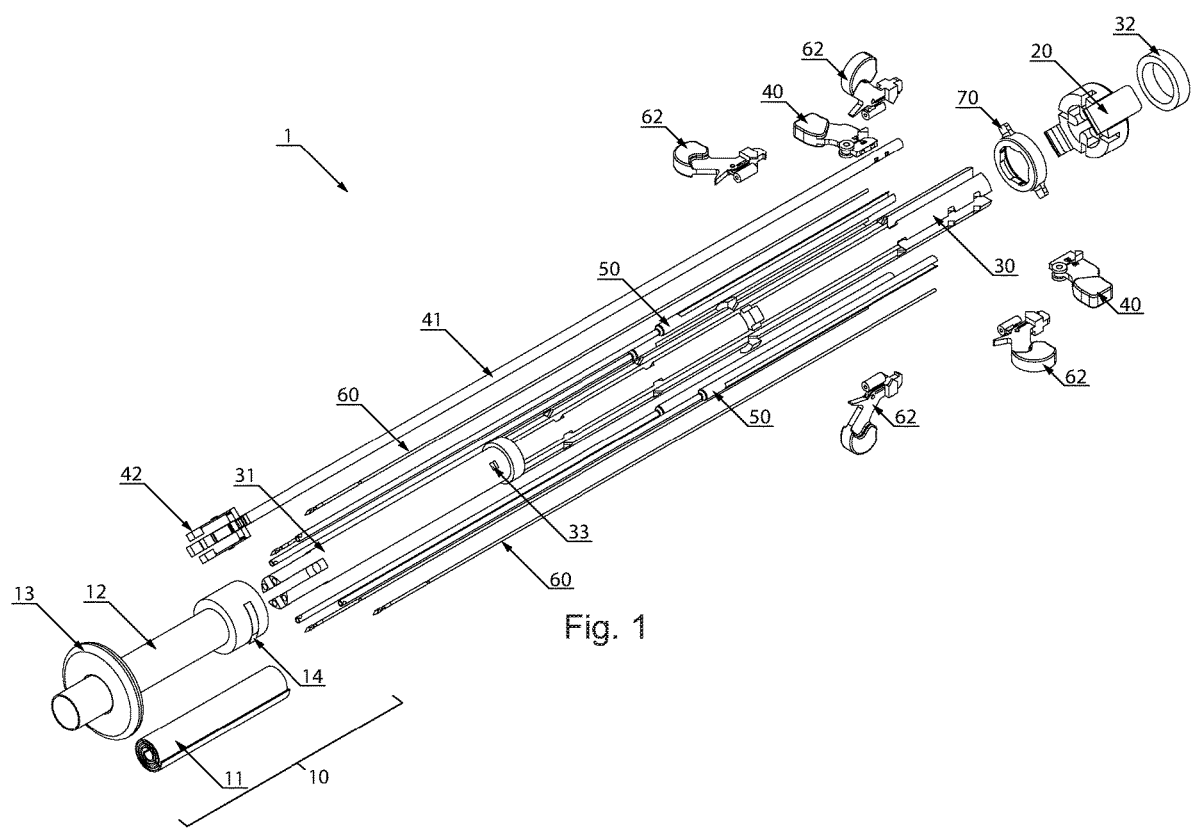
FIG. 1 is an exploded view of a hernia repair device according to an exemplary embodiment of the present invention.

FIG. 1 is an exploded view of a hernia repair device, generally designated by reference number 1, according to an exemplary embodiment of the present invention. The hernia repair device 1 includes a mesh cartridge 10 that is made up of a generally cylindrical cartridge housing 12 and a proximal flange 13 moveably positioned on the housing 12. The cartridge housing 12 is of suitable shape and size to house a rolled up hernia repair mesh 11. As explained in detail below, the hernia repair mesh 11 may be deployed through an open end of the cartridge housing 12 and placed and fixed into position using the various components of the hernia repair device 1.

The mesh cartridge 10 is attached to a main housing 30 of the hernia repair device 1. In this regard, the main housing 30 is arranged coaxially with the mesh cartridge 10, with a distal end portion of the main housing 30 extending into the mesh cartridge 10. The mesh cartridge 10 includes a detent mechanism 14 that is manipulated by a user to lock and unlock the mesh cartridge 10 from the main housing 30. When the detent mechanism 14 is in the unlocked configuration, the main housing 30 is able to slide relative to the mesh cartridge 10.

Figure 2:
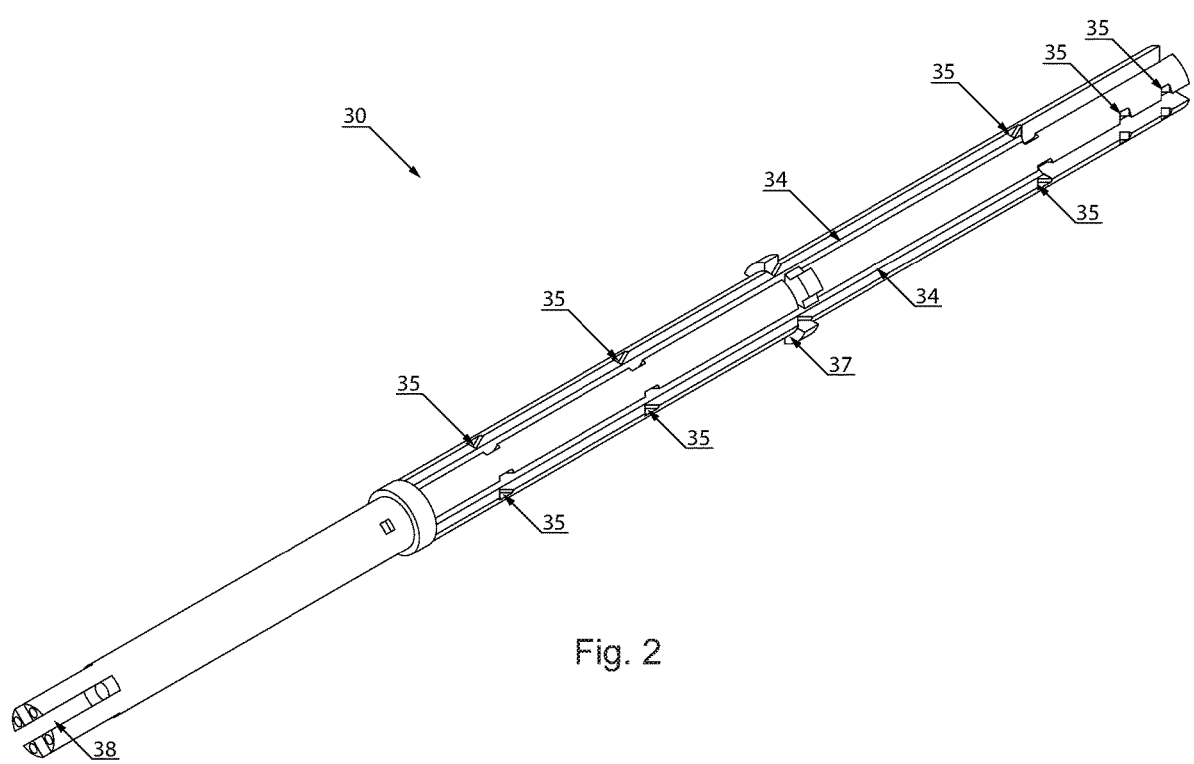
FIG. 2 is a perspective view of a main housing of a hernia repair device according to an exemplary embodiment of the present invention.

As shown in FIG. 2, the main housing 30 is a generally cylindrical structure that includes a plurality of longitudinal slots 34 positioned equidistantly around the perimeter of the main housing 30. The longitudinal slots 34 extend from a proximal end of the main housing 30 to an intermediate position between the proximal and distal end portions of the main housing 30. Each longitudinal slot 34 includes a plurality of widened portions that form a plurality of laterally extending locking slots 35 disposed along the length of the main housing 30. Stops 37 extend outwards between the longitudinal slots 34 at an intermediate portion of the main housing 30. A locking ring 32 is disposed at the proximal end of the main housing 30 to close off the otherwise open ends of the longitudinal slots 34. The main housing 30 also includes distal longitudinal slots 38 formed at the distal end portion of the main housing 30. The length of the main housing 30 may be in the range of 300 mm to 400 mm, and in an exemplary embodiment is 330 mm, and the diameter of the distal end portion of the main housing 30 (i.e., the portion of the main housing 30 intended for insertion into the patient) may be in the range of 10 mm to 20 mm, and in an exemplary embodiment is 15 mm. In general, the diameter at any point along the length of the main housing 30 preferably does not exceed 25 mm.

The main housing 30 also includes a first distal slot 31 and a more proximal positioned, second distal slot 33 into which the detent mechanism 14 of the mesh cartridge 10 extends to lock the mesh cartridge 10 in position. Specifically, in an initial configuration, the detent mechanism 14 extends into the first distal slot 31 so that the mesh cartridge 10 is locked in position over the distal end of the main housing 30. During use of the hernia repair device 1, a button associated with the detent mechanism 14 may be depressed to unlock the mesh cartridge 10 from its initial position. The mesh cartridge 10 may then be slid along the main housing 30 in the proximal direction, resulting in the hernia mesh 11 being pushed out of the mesh cartridge 10 by the distal end of the main housing 30. Sliding of the mesh cartridge 10 may continue until the detent mechanism 14 locks into the second distal slot 33, at which point the hernia mesh 11 is deployed and the distal end of the main housing 30 is exposed.

Figure 3:
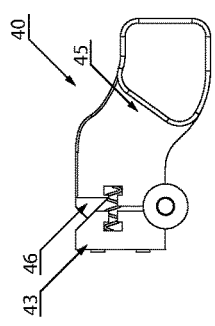
FIG. 3 is a plan view of a distal flange switch of a hernia repair device according to an exemplary embodiment of the present invention.

A central shaft 41 extends through the main housing 30 and includes at its distal end a distal flange 42. The distal flange 42 is activated by operation of distal flange switches 40, with each distal flange switch 40 extending through a corresponding one of two longitudinal slots 34 in the main housing 30. As shown in FIG. 3, each distal flange switch 40 includes a first portion 43 fixed to the central shaft 41 and a second portion 45 pivotally attached to the first portion 43 and extending through the corresponding longitudinal slot 34. The second portion 45 includes a central shaft detent 47 that is biased inwards by a central shaft spring mechanism 46 to lock the central shaft 41 in position. Specifically, in the locked position, the central shaft detent 47 extends into one of the plurality of locking slots 35 of the corresponding longitudinal slot 34. The central shaft 41 may be unlocked by application of force downwards on the second portion 45 of the distal flange switch 40, which results in pivoting of the detent mechanism 47 outwards to thereby disengage the central shaft detent 47 from the locking slot 35. A clinician may then slide distal flange switches 40 away from the proximal end portion towards a distal end portion of the main housing 30, resulting in corresponding movement of the central shaft 41 towards the distal end portion of the main housing 30 and deployment of the distal flange 42. In an exemplary embodiment, each distal flange switch 40 is adjustable between a first one of the locking slots 35 and a second, more distally positioned one of the locking slots 35, so that when the distal flange switch 40 is locked at the second locking slot 35, the distal flange 42 is fully deployed.

The length of the central shaft 41 may be in the range of 300 mm to 400 mm, and in an exemplary embodiment is 330 mm. According to an exemplary embodiment, the outer diameter of the central shaft 41 is within the range of 2 mm and 5 mm and the inner diameter of the central shaft 41 is within the range of 1 mm and 4 mm.

Figure 4A:
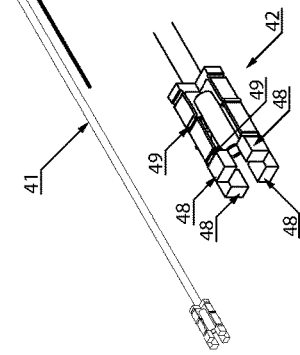
FIGS. 4A and 4B show different configurations of a distal flange of a hernia repair device according to an exemplary embodiment of the present invention.
Figure 4B:
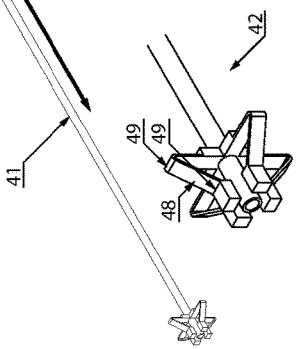

As shown in FIGS. 4A and 4B, the distal flange 42 includes longitudinally extending prongs 48 aligned with the distal longitudinal slots 38 of the main housing 30. The distal end portion of each prong 48 is fixed to the inner surface of the main housing 30, and each prong 48 includes kinked portions 49. In the deployed configuration shown in FIG. 4B, the central shaft 41 has been slid downwards towards the distal end portion of the main housing 30, resulting in application of a bending force to the prongs 48 via the fixed distal end portions and the kinked portions 49. This results in each prong 48 folding outwards and protruding from the corresponding distal longitudinal slot 38 of the main housing 30.

The central shaft 41 is preferably a hollow structure so that, in accordance with an exemplary embodiment, a camera may be introduced through the central shaft 41 and positioned between the hernia mesh and underside of the abdominal wall. Alternatively, the central shaft 41 may be used to introduce pressurized gas to assist with opening the hernia mesh material.

Four suture needle ports 50 extend through the main housing 30 and are controlled by a suture needle port switch 20. Specifically, sliding of the suture needle port switch 20 towards the distal end portion of the main housing 30 results in deployment of all four suture needle ports 50 from the main housing 30, while sliding of the suture needle port switch 20 towards the proximal end portion of the main housing 30 results in retraction of the suture needle ports 50.

Figure 5A:
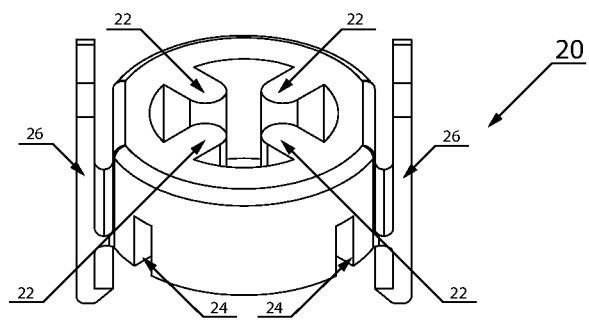
FIG. 5A is a perspective view of a suture needle port switch of a hernia repair device according to an exemplary embodiment of the present invention.
Figure 5B:
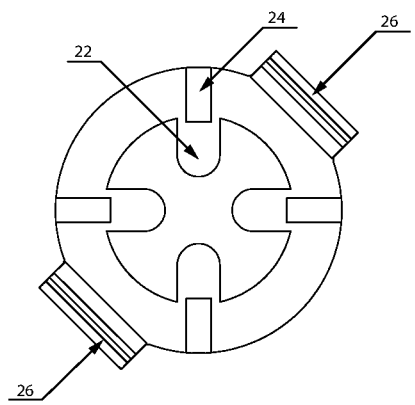
FIG. 5B is a plan view of the suture needle port switch of FIG. 5A.

FIGS. 5A and 5B shows the suture needle port switch 20 in more detail. The suture needle port switch 20 is a generally cylindrical structure with an open interior to allow passage of the central shaft 41. The suture needle port switch 20 includes radially extending portions 22 each protruding into a corresponding one of the longitudinal slots 34 and configured for attachment (e.g., by heat sealing, welding or glue or other adhesive) to a proximal end portion of a corresponding suture needle port 50. Longitudinally extending slots 24 are disposed around the perimeter of the suture needle port switch 20 for engagement with suture needle switches 62 disposed below the suture needle port switch 20 (i.e., at a more distal position relative to the suture needle port switch 20). The suture needle port switch 20 further includes a pair of longitudinally extending handles 26 that may be used by a clinician to grip the suture needle port switch 20 and move the suture needle port switch 20 into position along the main housing 30. In this regard, depressing the proximal end portions of the handles 26 cause the handles 26 to flex so that the distal end portions of the handles 26 can be locked into engagement with the stops 37 of the main body 30.

Figure 6:
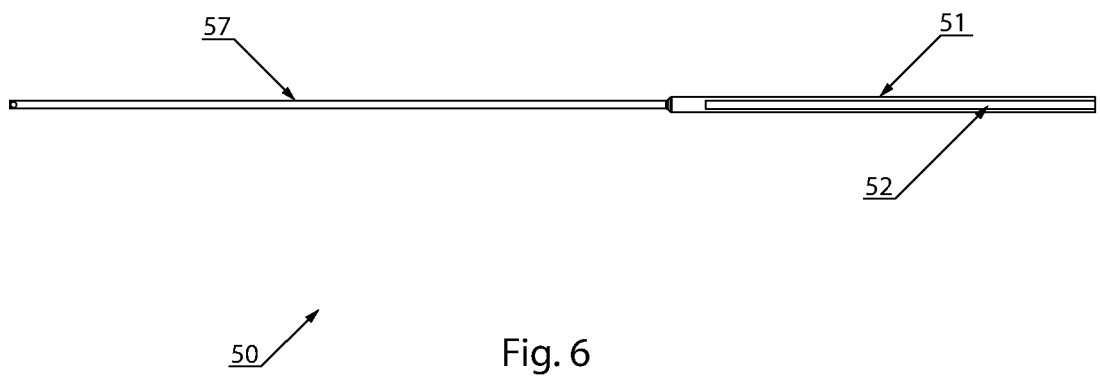
FIG. 6 is a plan view of a suture needle port of a hernia repair device according to an exemplary embodiment of the present invention.

As shown in FIG. 6, each suture needle port 50 includes a proximal end portion 51 and a distal end portion 57. The proximal end portion 51 includes a longitudinally extending suture needle access slot 52. The proximal end portion 51 preferably has a diameter that is larger than that of the distal end portion 57.

The hernia repair device 1 also includes four suture needles 60, with each suture needle 60 extending through a corresponding one of the four suture needle ports 50. Specifically, each suture needle 60 is arranged coaxially with and slidable relative to the corresponding suture needle port 50. Each suture needle 60 is attached to and individually controlled by a corresponding suture needle switch 62. Sliding of one of the suture needle switches 62 away from the proximal end portion towards the distal end portion of the main housing 30 results in movement of the corresponding suture needle 60 towards the distal end portion of the main housing 30. As explained in more detail below, the suture needle switches 62 are controlled to individually deploy the suture needles 60 from their corresponding suture needle ports 50 so that, in turn, the hernia mesh can be properly positioned and anchored.

Figure 7A:
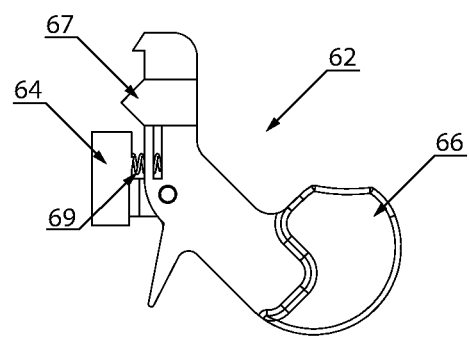
FIG. 7A is a plan view of a suture needle switch of a hernia repair device according to an exemplary embodiment of the present invention.
Figure 7B:
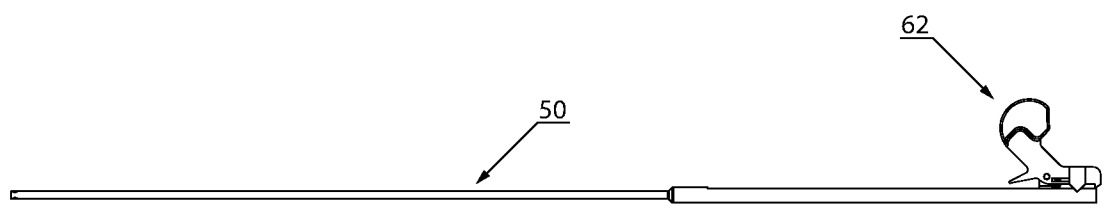
FIG. 7B is a suture needle port and associated suture needle switch of a hernia repair device according to an exemplary embodiment of the present invention.

As shown in FIG. 7A, each suture needle switch 62 includes a first portion 64 fixed to a corresponding suture needle 60 and a second portion 66 pivotally attached to the first portion 64 and extending through the corresponding suture needle access slot 52 (FIG. 7B) and a corresponding one of the longitudinal slots 34 of the main body 30. The second portion 66 includes a suture needle detent 67 that is biased inwards by a suture needle spring mechanism 69 to lock the suture needle 60 in position. Specifically, in the locked position, the suture needle detent 67 extends into one of the plurality of locking slots 35 of the corresponding longitudinal slot 34. The suture needle 60 may be unlocked by application of force downwards on the second portion 66 of the suture needle switch 60, which results in pivoting of the suture needle detent 67 outwards to thereby disengage the suture needle detent 67 from the locking slot 35. A clinician may then slide the suture needle switches 62 towards the distal end portion of the main housing 30, resulting in corresponding movement of the suture needle 60 towards the distal end portion of the main housing 30. When the suture needle ports 50 are locked in their furthest distal position, the suture needle switches 62 allow for individual and independent movement of the suture needles 60 and deployment of the suture needles 60 from their corresponding suture needle port 50.

A quick release ring 70 is disposed on the main housing 30 at a more distal position relative to the suture needle port switch 20 and the suture needle switches 62. Sliding the quick release ring 70 towards the proximal end portion of the main housing 30 results in simultaneous retraction of the suture needles 60 into the suture needle ports 50 and the suture needle ports 50 into the main housing 30 after completion of the hernia repair procedure.

Operation of the hernia repair device will now be described with reference to FIGS. 8 to 16.

Figure 8:
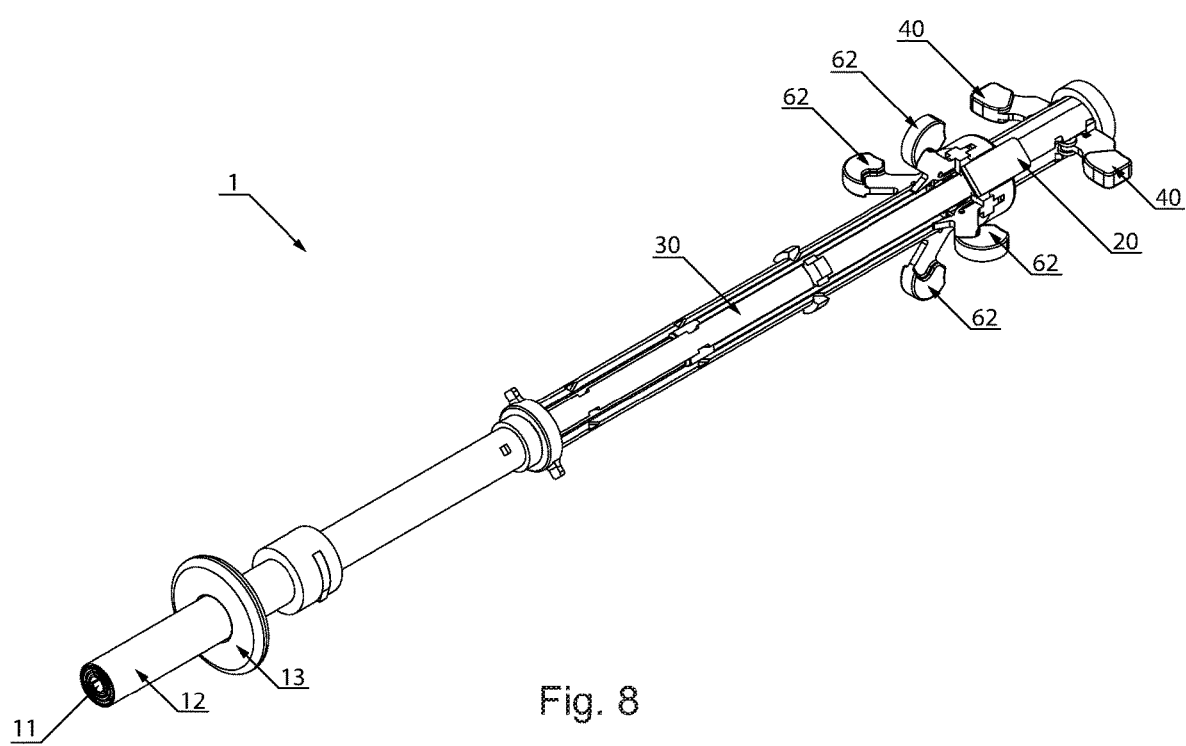
FIG. 8 is a perspective view of a hernia repair device as configured during a hernia repair procedure according to an exemplary embodiment of the present invention.

FIG. 8 shows the hernia repair device 1 prior to use. In this configuration, the hernia mesh 11 is enclosed in the cartridge housing 12, the cartridge housing 12 is attached to the main housing 30, the hernia mesh 11 is connected to the suture needles 60 located within the main housing 30 and the suture needle switches 62, the suture needle port switch 20 and the distal flange switch 40 are fully retracted towards the distal end portion of the main housing 30.

Figure 9:
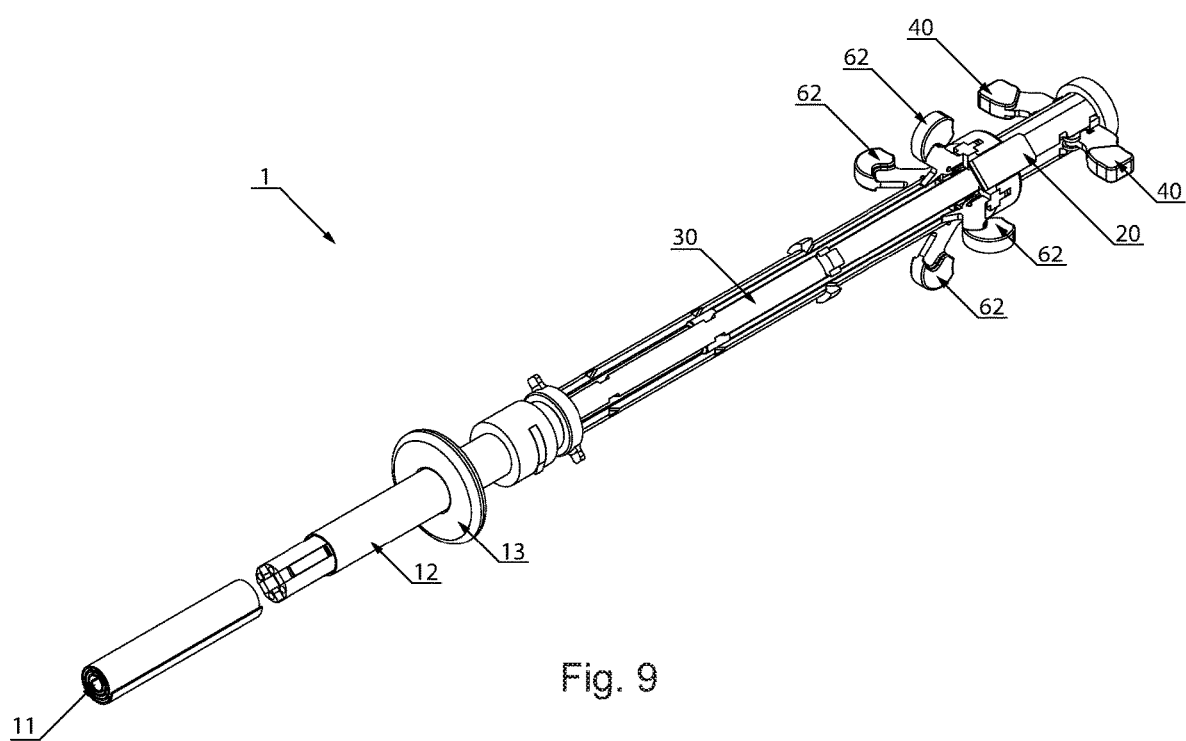
FIG. 9 is a perspective view of a hernia repair device as configured during a hernia repair procedure according to an exemplary embodiment of the present invention.

FIG. 9 shows the hernia repair device 1 after the main body 30 has been telescoped into the mesh cartridge 10 to push the hernia mesh 11 clear of the cartridge housing 12. Suture lines (not shown) attach the hernia mesh material to the suture needles 60. In this configuration, the suture needles 60 are housed within the suture needle ports 50 within the main housing 20. Once the hernia mesh 11 is deployed from the cartridge housing 12, the hernia mesh 11 unfurls within the abdominal cavity and aligns to the hernia site. The clinician may align the hernia mesh 11 through adjustment in orientation of the hernia repair device 1 and, if necessary, manipulation by laparoscopic instruments.

Figure 10A:
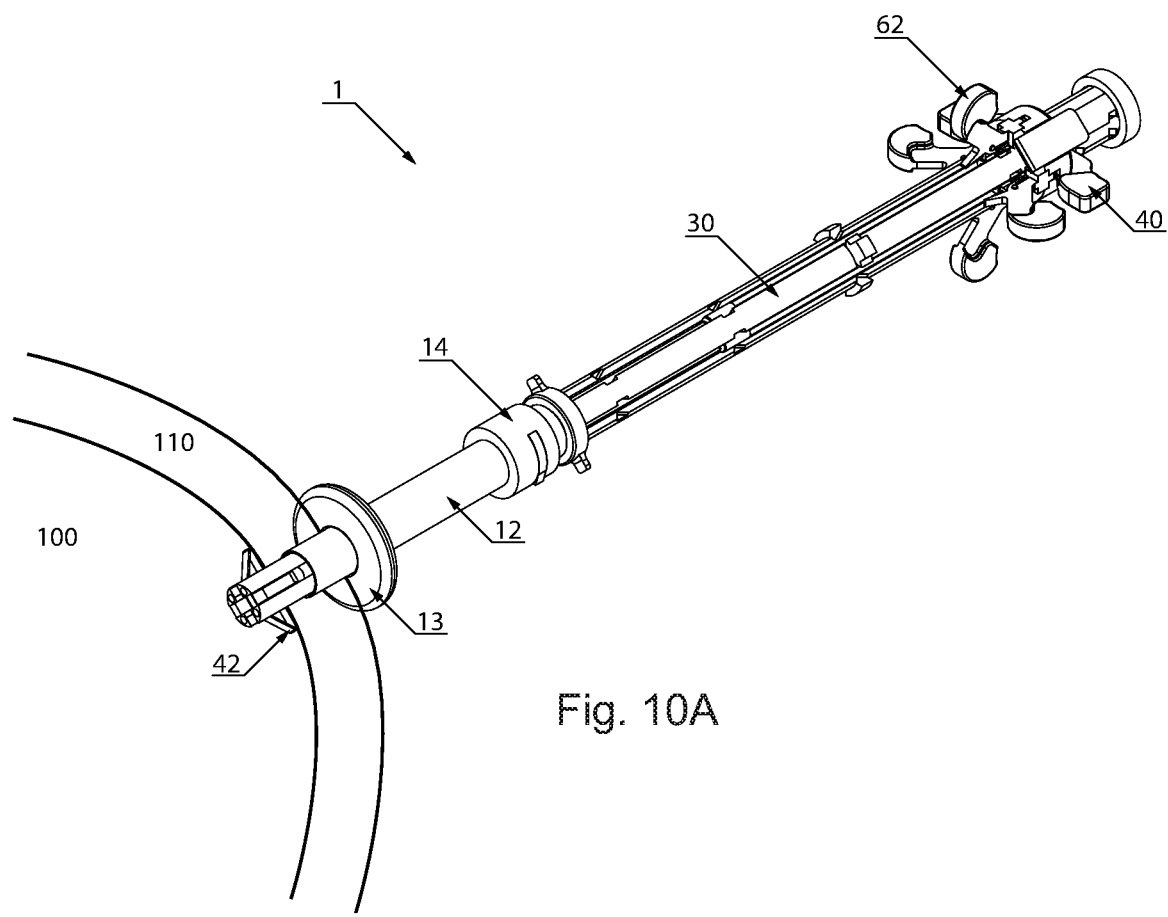
FIG. 10A is a perspective view of a hernia repair device as configured during a hernia repair procedure according to an exemplary embodiment of the present invention.

FIG. 10A shows the device 1 as inserted within the abdominal cavity 100 of a patient. The cartridge housing 30 is inserted through an incision in the abdominal wall 110, central to the hernia site. In this configuration, the cartridge locking button 14 is depressed to prevent movement of the cartridge housing 12 relative to the main housing 30 after the hernia mesh 11 is discharged into the abdominal cavity. Next, the distal flange switch 40 is depressed and slid down the main housing in the distal direction. This action deploys the distal flange 42 while progressing the central shaft 41 toward the distal end of the main housing 30. The main housing 30 (now locked to the mesh cartridge 10) is pulled upward so that the distal flange 42 touches the underside of the abdominal wall 110. The proximal flange 13 is moved down the cartridge housing 12 until the proximal flange 13 is moved flush with the patient's skin. The result of these operations is that the abdominal wall 110 is sandwiched between the distal flange 42 and the proximal flange 13, thereby anchoring the hernia repair device 1 in position at the hernia site.

Figure 10B:
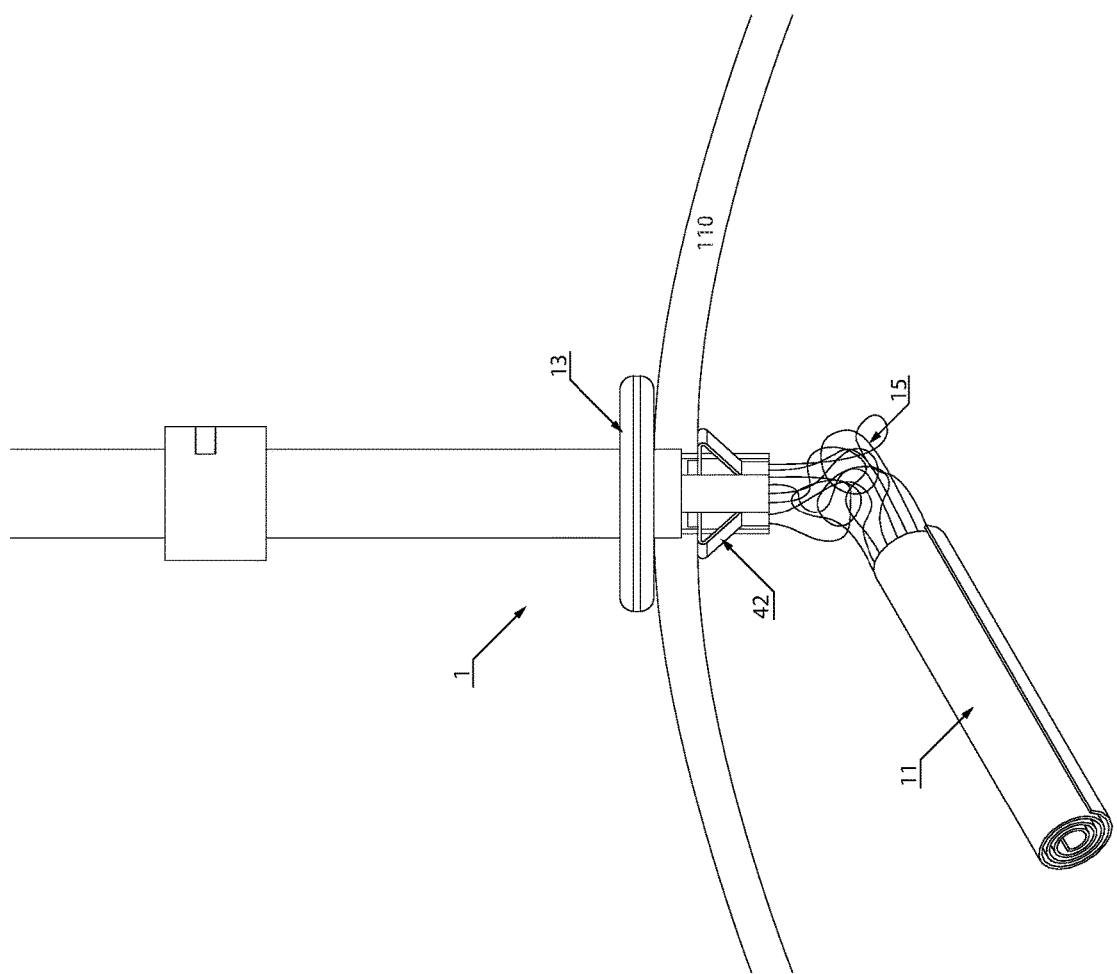
FIG. 10B shows a portion of a hernia repair device extending through a patient's abdomen during a hernia repair procedure according to an exemplary embodiment of the present invention.

FIG. 10B shows the state of the hernia mesh 11 and hernia repair device 1 after the steps described in regards to FIGS. 9 and 10A. The hernia mesh 11 is deployed but not yet unfurled, and the suture lines 15 (eight in total) are in a slack state.

Figure 11A:
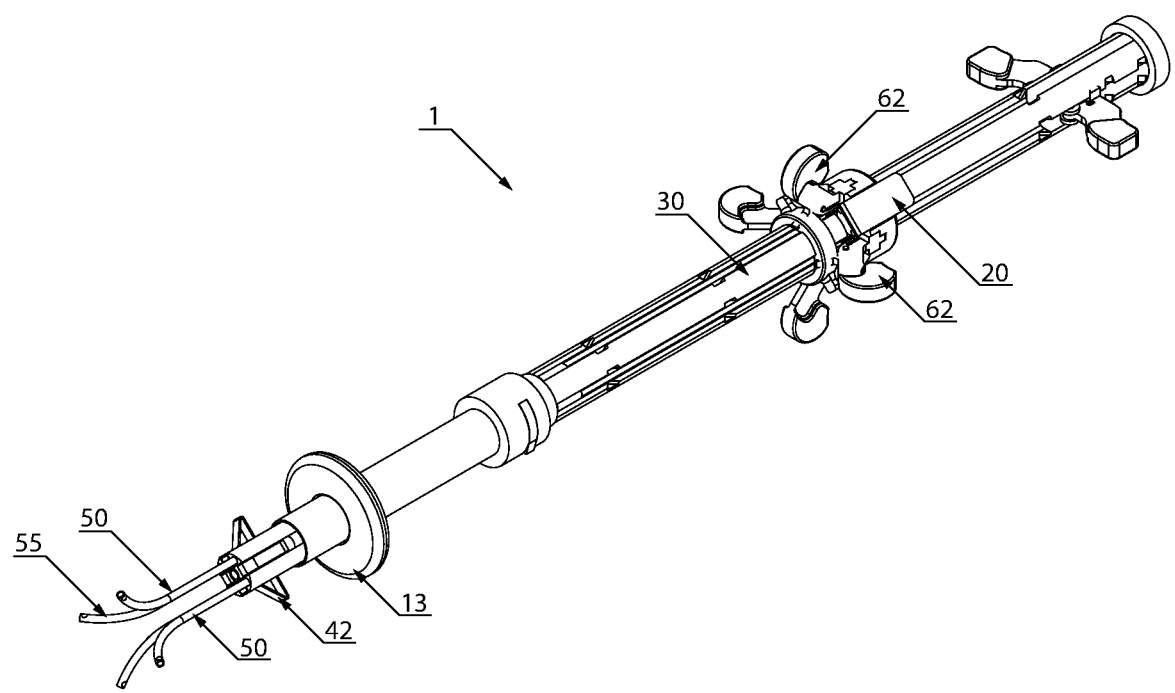
FIG. 11A is a perspective view of a hernia repair device as configured during a hernia repair procedure according to an exemplary embodiment of the present invention.
Figure 11B:
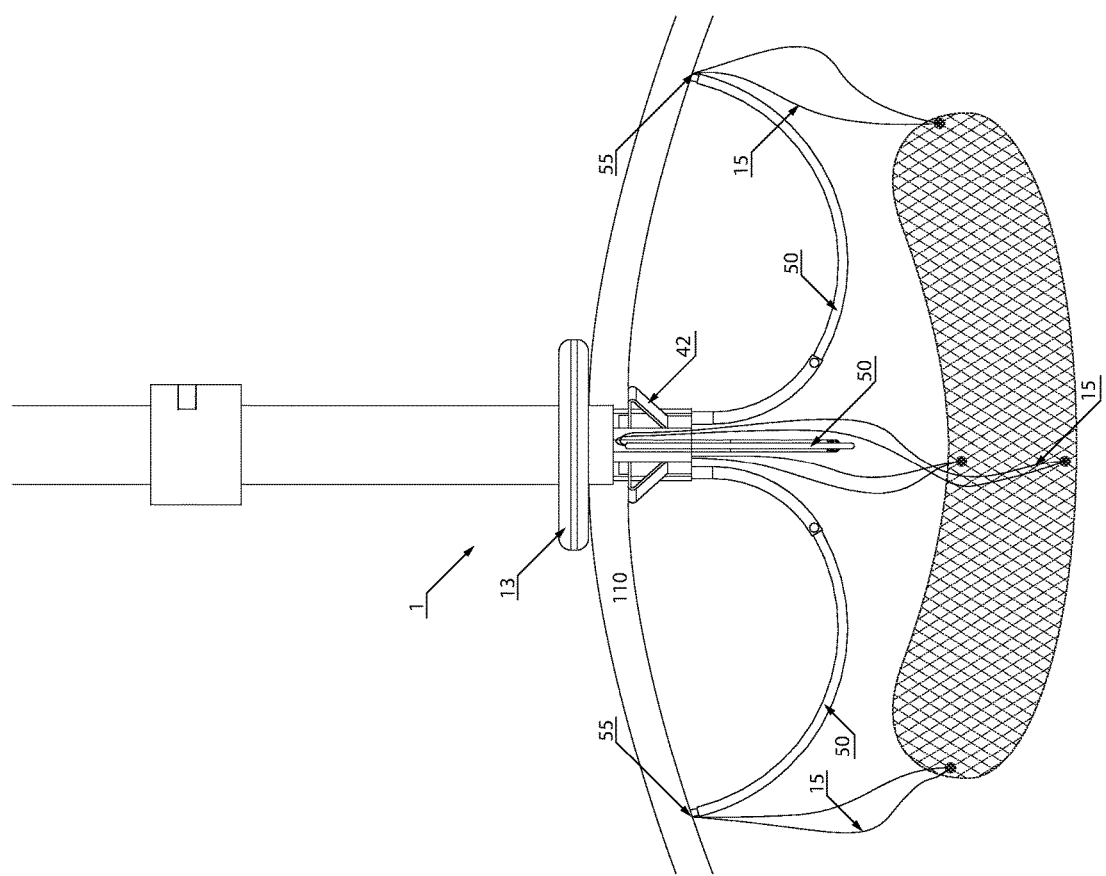
FIG. 11B shows a portion of a hernia repair device extending through a patient's abdomen during a hernia repair procedure according to an exemplary embodiment of the present invention.

Next, as shown in FIG. 11A, the suture needle port switch 20 is depressed and slid distally along the main housing 30. This motion causes the four suture needle ports 50 to deploy clear of the main housing 30. At this stage, as shown in FIG. 11B, the tips of the suture needle ports 50 are located at the underside of the abdominal wall 110, the hernia mesh 11 is beginning to unfurl and the suture lines 15 are still somewhat slack.

In an exemplary embodiment, each of the suture needle ports 50 have light emitting diodes (LEDs) 55 housed within the distal tip of the suture needle port 50 so that locations of the suture needle ports 50 within the patient's body are more visible to the clinician. Specifically, the LEDs 55 assist the clinician in confirming that the hernia repair device 1 is correctly oriented and that the suture needles 60 will exit through the patient's skin at the required exit points. Alternatively, LEDs may be located at the distal tips of the suture needles 60. It should be appreciated that other types of light sources may be used, such as, for example, fiber optic light sources.

Figure 12A:
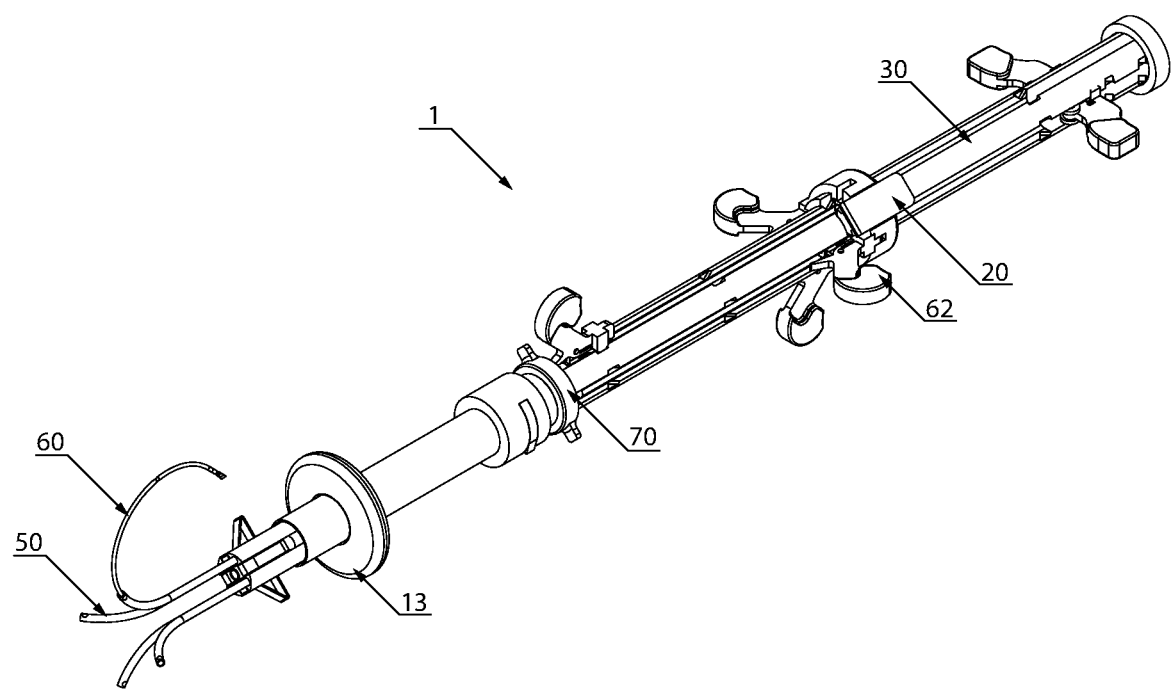
FIGS. 12A-12C are perspective views of a hernia repair device as configured during various steps of a hernia repair procedure according to an exemplary embodiment of the present invention.
Figure 12B:
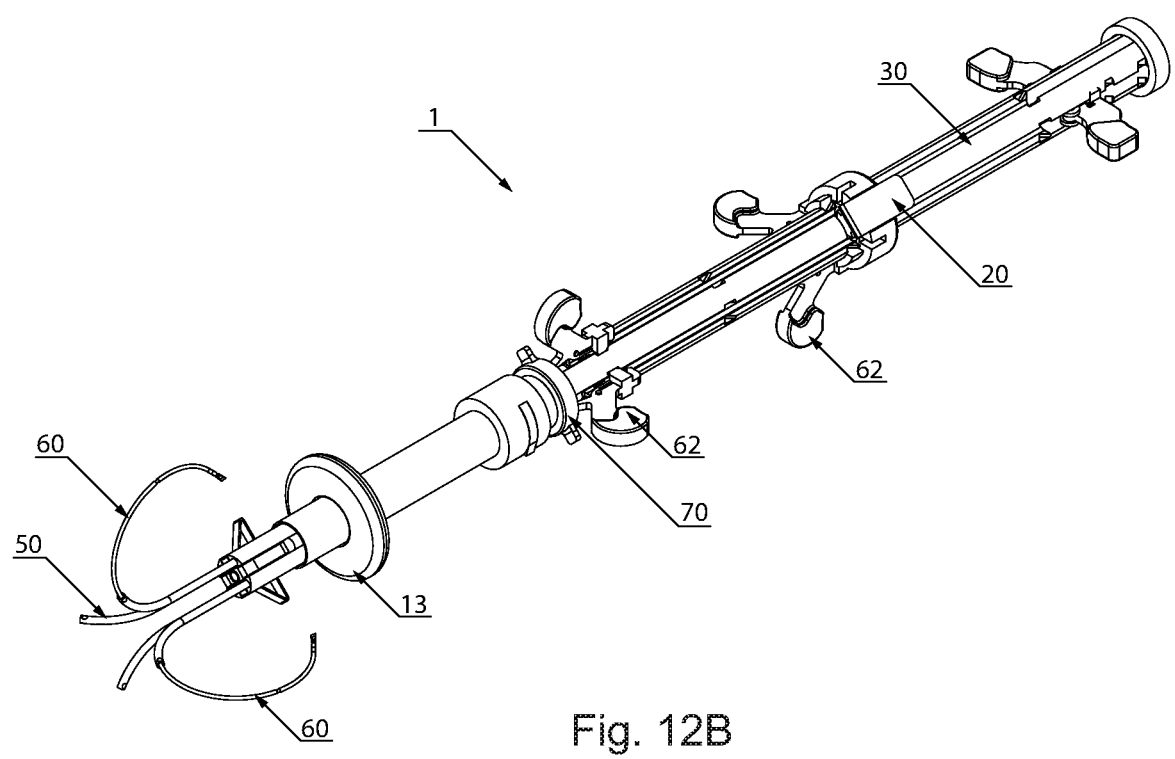
Figure 12C:
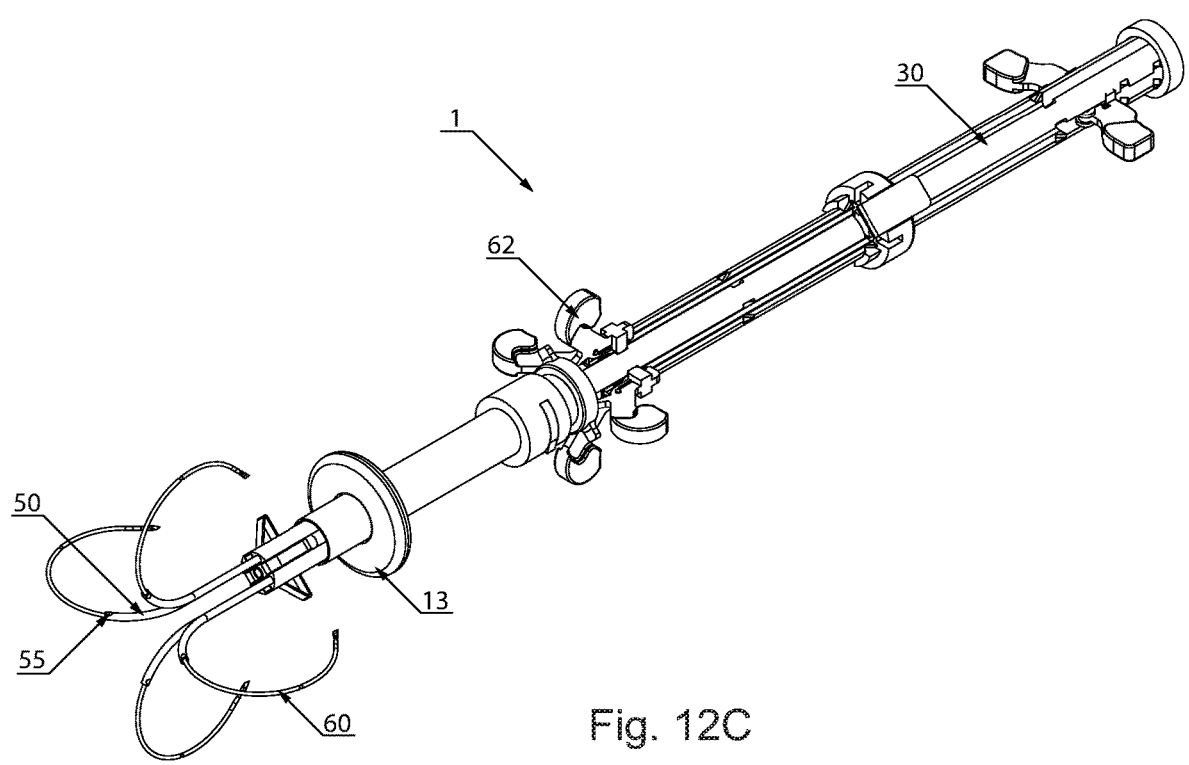

Next, as shown in FIGS. 12A, 12B and 12C, the suture needles 60 are deployed from their corresponding suture needle ports 50. Specifically, each suture needle switch 62 is depressed and slid distally along the main housing 30, which causes a corresponding one of the suture needles 60 to deploy from its suture needle port 50 and through the abdominal wall 110 to exit through the patient's skin. The corresponding suture line is then clamped and cut from the suture needle 60. The suture needle 60 is then retracted by sliding suture needle switch 62 proximally along the main housing 30. Next, the clinician moves the patient's skin (e.g., approximately 1 mm to 2 mm) and the same suture needle 60 is deployed once again so as to protrude through the original exit site, and the suture material is again clamped and cut. This process is completed for the other three suture needles 60, leaving the eight suture lines clamped outside the patient's body with the suture needles 60 protruding from the individual exit points. FIG. 12A shows one suture needle 60 deployed, FIG. 12B shows two suture needles 60 deployed and FIG. 12C shows all suture needles 60 deployed at which point all suture lines have exited the body and have been clamped off. The clinician can now start to maneuver the hernia mesh 11 towards the underside of the abdominal wall 110.

Figure 12D:
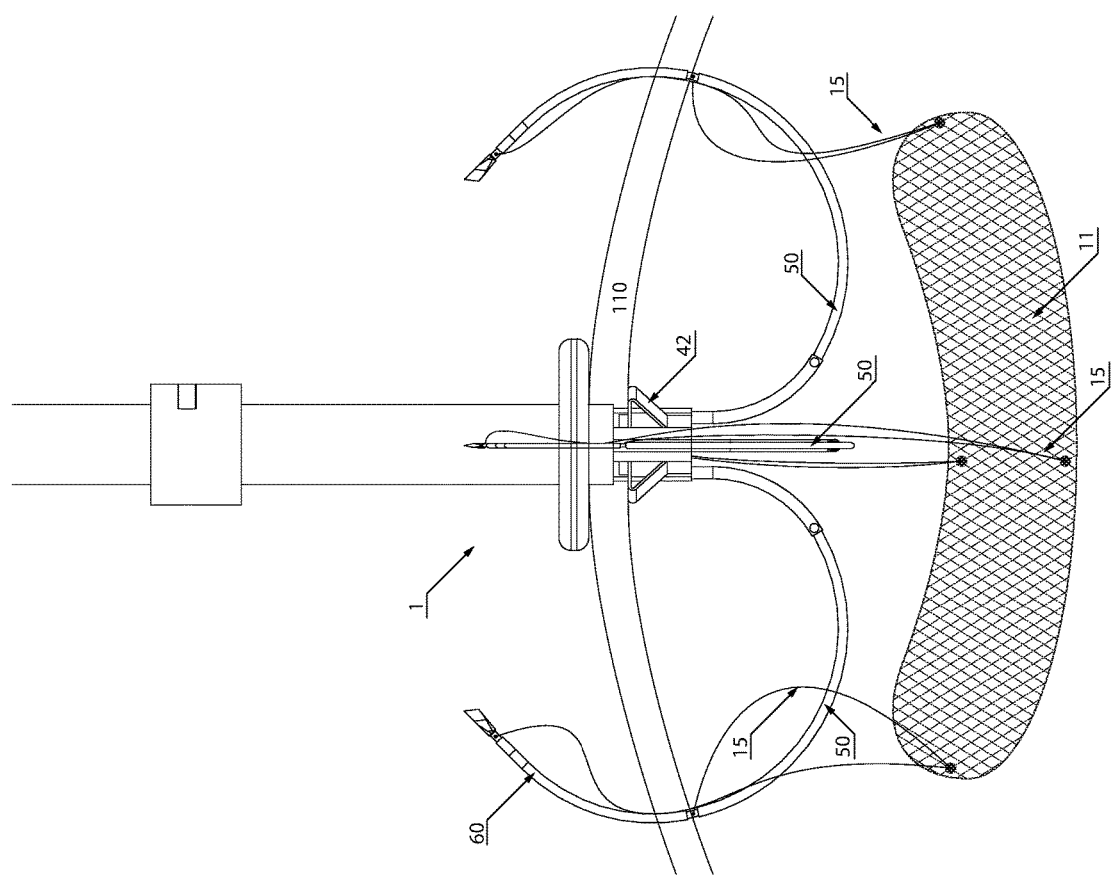
FIG. 12D shows a portion of a hernia repair device extending through a patient's abdomen during a hernia repair procedure according to an exemplary embodiment of the present invention.

FIG. 12D shows the configuration of the hernia repair device 1 and associated hernia mesh 11 after the procedures described above with reference to FIGS. 12A-12C (although prior to cutting and clamping of the suture lines). Specifically, FIG. 12D shows the suture needles 60 pierced through the abdominal wall 110 and outer skin (for clarity, a large gap is shown between the suture lines 15 within each pair, although it should be appreciated that the suture lines 15 within each pair exit the same point as the corresponding suture needle 60), the hernia mesh 11 completely unfurled and the suture lines 15 now in tension. The hernia mesh 11 is moved into location by pulling on the now accessible suture lines 15. FIG. 12D also depicts the proposed locations where the suture lines 15 are attached to the hernia mesh 11. In this regard, the hernia mesh 11 may have any suitable shape profile, such as, for example, rectangular or square.

Figure 13:
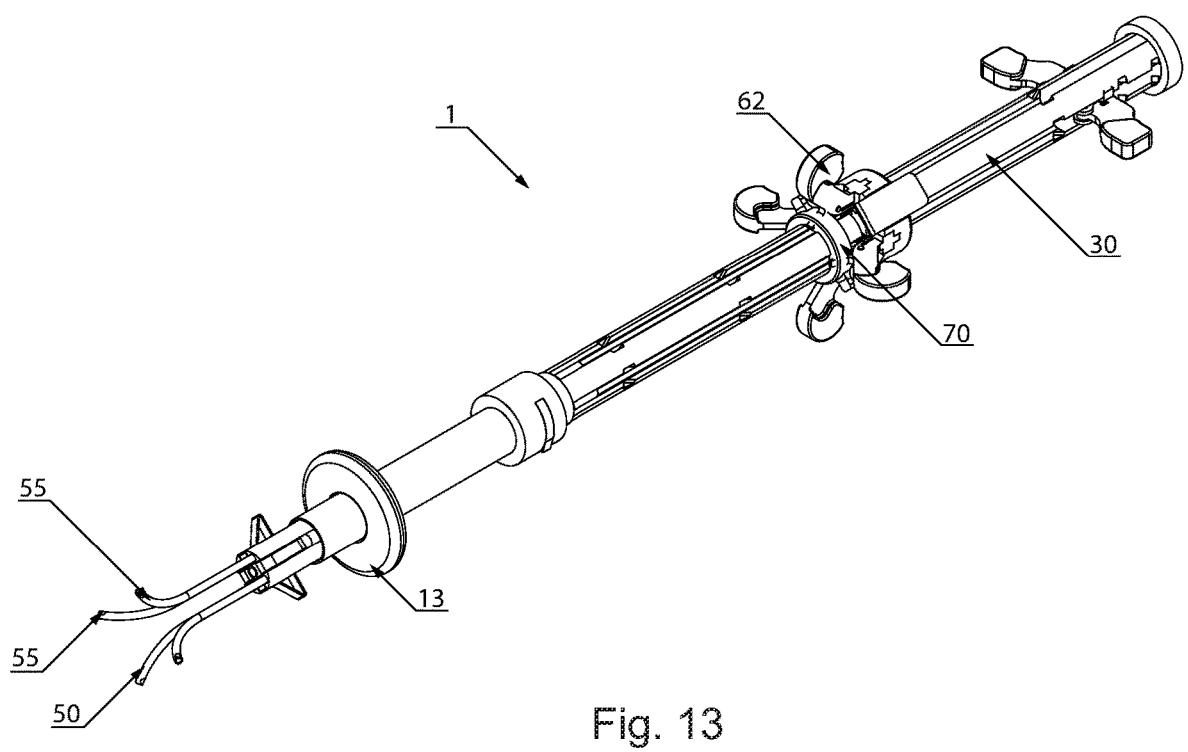
FIG. 13 is a perspective view of a hernia repair device as configured during a hernia repair procedure according to an exemplary embodiment of the present invention.

The next steps involve retraction of the suture needles 60 and suture needle ports 50 so that the hernia repair device 1 can be removed from the abdominal cavity. The clinician may grip the main housing 30 with the non-dominant hand and use the dominant hand to slide the quick release ring 70 upwards (i.e., towards the proximal end portion of the main housing 30) under the four suture needle switches 62. This results in sliding of the suture needle switches 62 simultaneously in the proximal direction until they engage with the suture needle port switch 20, which in turn retracts the suture needles 60 simultaneously into the suture needle ports 50. At this point, as shown in FIG. 13, the hernia repair device 1 is still located within the incision site and the hernia mesh 11 has been moved up towards the underside of the abdominal wall.

Figure 14:
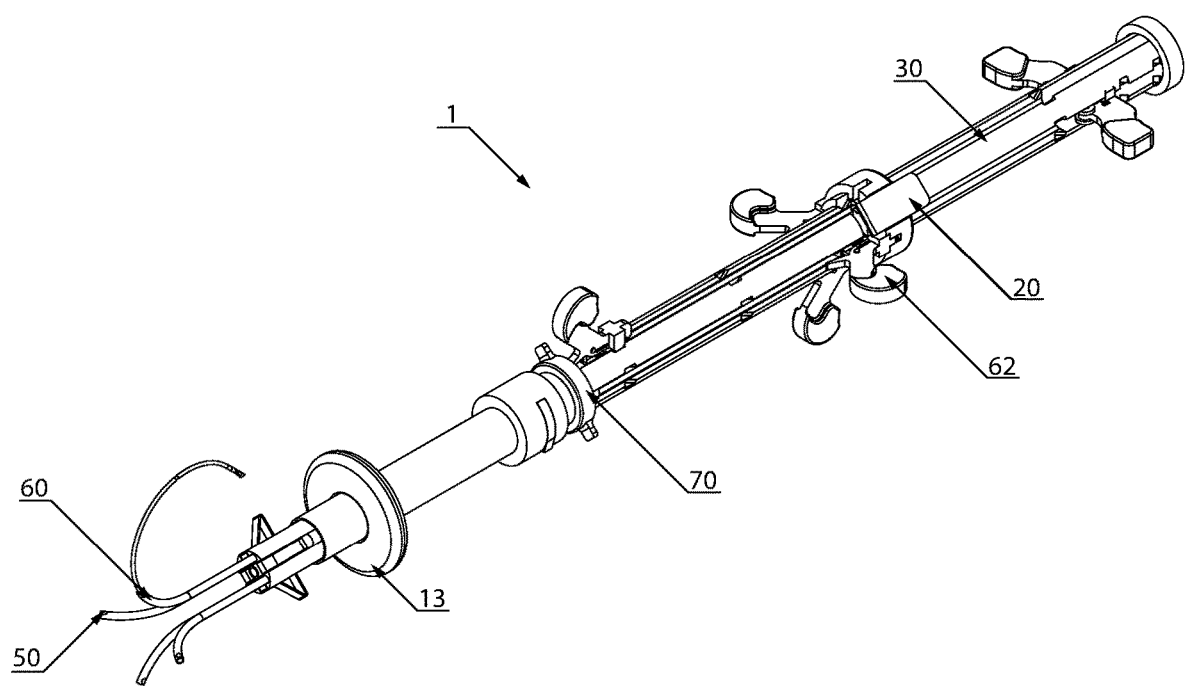
FIG. 14 is a perspective view of a hernia repair device as configured during a hernia repair procedure according to an exemplary embodiment of the present invention.

Alternatively, the suture needles 60 may be retracted individually using just the suture needle switches 62. In this regard, FIG. 14 shows three suture needle switches 62 retracted to the suture needle port switch 20.

Figure 15:
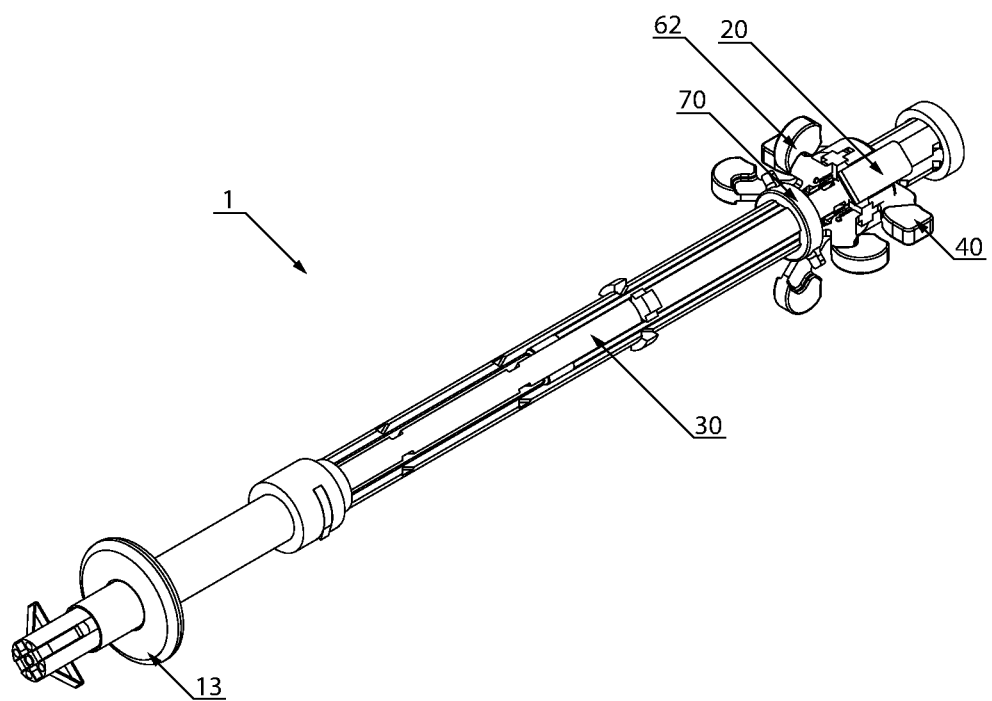
FIG. 15 is a perspective view of a hernia repair device as configured during a hernia repair procedure according to an exemplary embodiment of the present invention.

Next, as shown in FIG. 15, the suture needle ports 50 are retracted into the main housing 30. In this step, the handles 26 of the suture needle port switch 20 are depressed to unlock the suture needle switch 20 from the stops 37 of the main body 30, and the quick release ring 70 along with the suture needle switches 62 and the suture needle port switch 20 are pulled proximally along the main housing 30 until they contact the distal flange switch 40.

Figure 16:
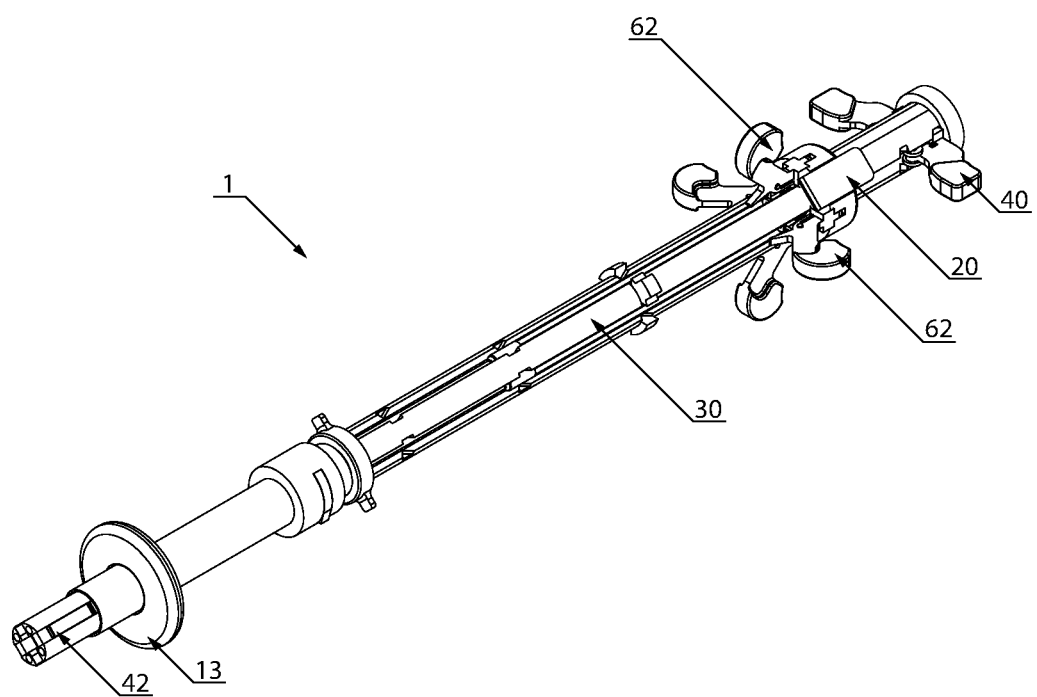
FIG. 16 is a perspective view of a hernia repair device as configured during a hernia repair procedure according to an exemplary embodiment of the present invention.

Next, as shown in FIG. 16, the distal flange 42 is retracted into the main housing 30 by disengaging the distal flange switch 42 and sliding it proximally to the top of the main housing 30. The central shaft 41 simultaneously retracts within the main housing 30. The hernia repair device 1 is then removed and the incision site is closed. At this point, the hernia mesh 11 is disposed at its final location on the underside of the abdomen.

Figure 17A:
FIG. 17A is a planar view of a suture needle according to an exemplary embodiment of the present invention.
Figure 17B:
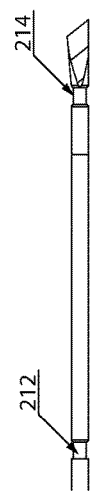
FIG. 17B is a detailed view of the tip portion of the suture needle of FIG. 17A.
Figure 18A:
FIG. 18A is a planar view of a suture needle according to an exemplary embodiment of the present invention.
Figure 18B:
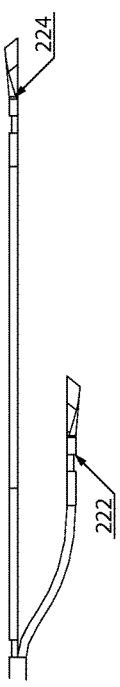
FIG. 18B is a detailed view of the tip portion of the suture needle of FIG. 18A.

According to an exemplary embodiment, the distal tip portion of the suture needles are double slotted or double barbed to secure the sutures from the hernia mesh. In this regard, FIGS. 17A and 17B show a double slotted suture needle 210 including a first slot 212 and a more distal second slot 214, and FIGS. 18A and 18B show a double barbed suture needle 220 including a first barb 222 and a more distal second barb 224. In an alternative embodiment, the suture needles 220 may include eyelets rather than slots.

According to an exemplary embodiment, the various switches of the hernia repair device 1, including the distal flange switches 40, the suture needle port switch 20 and the suture needle switches 62 are color-coded or otherwise labeled to indicate their functions. The LEDs 55 on the suture needle ports 50 (or on the suture needles 60) may also be color-coded consistent with the color-coding of the various switches.

Having described this invention with regard to specific embodiments, it is to be understood that the description is not meant as a limitation since further modifications and variations may be apparent or may suggest themselves to those skilled in the art. It is intended that the present application cover all such modifications and variations.

The invention claimed is:

1. A hernia repair device comprising:
a main body comprising a first longitudinally extending slot and a second longitudinally extending slot, each of the first and second longitudinally extending slots comprising a first widened portion that forms a first locking slot and a second widened portion that forms a second locking slot, the second locking slot disposed at a more distal position along the main body relative to the first locking slot;
a central shaft extending through the main body and comprising a retractable distal flange disposed at a distal end portion of the central shaft, the central shaft defining a central channel extending through the main body;
a pair of distal flange switches, each distal flange switch comprising:
a first portion fixed to the central shaft; and
a second portion pivotally attached to the first portion and extending through a corresponding one of the first and second longitudinally extending slots, the second portion comprising a detent portion that is biased inwards, wherein
the distal flange switch has a first locked configuration in which the detent portion protrudes into the first locking slot of the corresponding one of the first and second longitudinally extending slots,
the distal flange switch has a second locked configuration in which the detent portion protrudes into the second locking slot of the corresponding one of the first and second longitudinally extending slots,
adjustment of the distal flange switch from the first locked configuration to the second locked configuration results in deployment of the distal flange, and
adjustment of the distal flange switch from the second locked configuration to the first locked configuration results in retraction of the distal flange,
a plurality of suture needle ports that are adjustable between a first configuration in which the suture needle ports are housed entirely within the main body and a second configuration in which the suture needle ports partially extend from the distal end portion of the main body; and
a plurality of suture needles that are adjustable between a first configuration in which the suture needles are housed entirely within the plurality of suture needle ports and a plurality of second configurations in which the plurality of suture needles partially extend from distal end portions of the plurality of suture needle ports; and
a hernia mesh attached to the plurality of suture needles.

2. The hernia repair device of claim 1, further comprising:
a suture needle port switch slideably disposed on the main body and attached to the plurality of suture needle ports so that movement of the suture needle port switch along the main body results in adjustment of the plurality of suture needle ports between the first and second configurations.

3. The hernia repair device of claim 1, wherein the main body further comprises a number of additional longitudinally extending slots so that a total number of longitudinally extending slots in the main body is equal to a number of suture needles that make up the plurality of suture needles.

4. The hernia repair device of claim 3, wherein each of the first and second longitudinally extending slots comprise a third widened portion that forms a third locking slot and a fourth widened portion that forms a fourth locking slot, the fourth locking slot disposed at a more distal position along the main body relative to the third locking slot.

5. The hernia repair device of claim 4, wherein each additional longitudinally extending slot comprises a first widened portion that forms a first locking slot and a second widened portion that forms a second locking slot, the second locking slot of each additional longitudinally extending slot disposed at a more distal position along the main body relative to the first locking slot of each additional longitudinally extending slot.

6. The hernia repair device of claim 5, further comprising a plurality of suture needle locking slots which include the third and fourth locking slots of the first and second longitudinally extending slots and the first and second locking slots of the additional longitudinally extending slots.

7. The hernia repair device of claim 6, wherein each of the plurality of suture needle ports comprises a suture needle access slot.

8. The hernia repair device of claim 7, further comprising:
a plurality of suture needle switches, each of the plurality of suture needle switches comprising:
a first portion fixed to a corresponding one of the suture needles; and
a second portion pivotally attached to the first portion and extending through the suture needles access slot of a corresponding one of the suture needle ports, the second portion comprising a detent portion that is biased inwards, wherein
the suture needle switch has a first locked configuration in which the detent portion protrudes into one of the suture needle locking slots of the corresponding one of the first, second and additional longitudinally extending slots,
the suture needle switch has a second locked configuration in which the detent portion protrudes into another one of the suture needle locking slots of the corresponding one of the first, second and additional longitudinally extending slots,
movement of the suture needle switch to the first locked configuration results in adjustment of the corresponding suture needle to one of the plurality of second configurations, and
movement of the suture needle switch to the second locked configuration results in adjustment of the corresponding suture needle to another one of the plurality of second configurations.

9. The hernia repair device of claim 1, wherein each of the plurality of suture needle ports comprises a light source disposed at a distal end portion of the suture needle port.

10. The hernia repair device of claim 9, wherein the light source is a light-emitting diode.

11. The hernia repair device of claim 1, further comprising a hernia mesh cartridge slideably attached to the main body and that houses the hernia mesh in a rolled-up configuration, wherein movement of the main body relative to the hernia mesh cartridge results in pushing of the hernia mesh from the hernia mesh cartridge to an unrolled deployed configuration.

12. The hernia repair device of claim 11, wherein the hernia mesh cartridge comprises a proximal flange that operates with the distal flange to anchor the hernia repair device in position.

13. The hernia repair device of claim 1, wherein the central channel is configured to direct pressurized gas to the hernia mesh.

14. The hernia repair device of claim 1, wherein the central channel is configured to direct a camera through the hernia repair device to a hernia repair site.

15. The hernia repair device of claim 1, further comprising a quick release mechanism disposed on the main body at a more distal position relative to the plurality of suture needle port switches and the plurality of suture needle switches, wherein movement of the quick release mechanism towards a proximal end portion of the main body results in simultaneous retraction of the plurality of suture needles into the plurality of suture needle ports and the plurality of the suture needle ports into the main body.

* * * * *